(12) United States Patent
Van Den Eede et al.

(10) Patent No.: US 8,580,362 B2
(45) Date of Patent: Nov. 12, 2013

(54) SILICONE PRODUCTS AND METHODS FOR MAKING SILICONE PRODUCTS

(75) Inventors: Thérèse Van Den Eede, Huise (BE); Bernard Hoste, Nazareth (BE)

(73) Assignee: Tricolast N.V., Deinze (BE)

( * ) Notice: Subject to any disclaimer, the term of this patent is extended or adjusted under 35 U.S.C. 154(b) by 1668 days.

(21) Appl. No.: 10/579,430

(22) PCT Filed: Nov. 17, 2004

(86) PCT No.: PCT/EP2004/013027
§ 371 (c)(1),
(2), (4) Date: May 15, 2006

(87) PCT Pub. No.: WO2005/048911
PCT Pub. Date: Jun. 2, 2005

(65) Prior Publication Data
US 2007/0093161 A1    Apr. 26, 2007

(30) Foreign Application Priority Data
Nov. 17, 2003    (NL) .................................... 1024793

(51) Int. Cl.
*B32B 23/00*    (2006.01)
*B32B 1/08*    (2006.01)

(52) U.S. Cl.
USPC ........ 428/34.1; 428/35.7; 428/35.9; 428/36.9

(58) Field of Classification Search
USPC .............................. 428/34.1, 35.7, 35.9, 36.9
See application file for complete search history.

(56) References Cited

U.S. PATENT DOCUMENTS

| 4,552,138 | A * | 11/1985 | Hofeditz et al. ............... 604/304 |
| 6,255,552 | B1 | 7/2001 | Cummings et al. |
| 6,324,703 | B1 * | 12/2001 | Chen .................................. 2/458 |
| 6,846,508 | B1 * | 1/2005 | Colas et al. ................... 427/2.31 |
| 7,304,202 | B2 * | 12/2007 | Sigurjonsson et al. ......... 602/58 |

FOREIGN PATENT DOCUMENTS

| DE | 198 29 712 | 1/2000 |
| EP | 0 147 588 | 7/1985 |
| WO | WO 02/45698 | 6/2002 |
| WO | WO 02/076519 | 10/2002 |

OTHER PUBLICATIONS

International Search Report dated May 12, 2005.

* cited by examiner

*Primary Examiner* — Marc Patterson
(74) *Attorney, Agent, or Firm* — Knobbe, Martens, Olson & Bear LLP (57) ABSTRACT

The present invention relates to a silicone product comprising a single or double elastic material which is covered along at least one surface with an adhesive or non-adhesive silicone-gel, wherein the elastic material is woven or knitted and comprises polyamide or polyester.

33 Claims, 3 Drawing Sheets

FIGURE 4

SILICONE PRODUCTS AND METHODS FOR MAKING SILICONE PRODUCTS

RELATED APPLICATIONS

This application is the U.S. National Phase under 35 U.S.C. §371 of International Application PCT/EP2004/013027, filed Nov. 17, 2004 which claims priority to NL 1024793, filed Nov. 17, 2003.

TECHNICAL FIELD OF THE INVENTION

The field of the invention lies in the medical, paramedical and cosmetic areas. The current invention relates to silicone products, and their use in, for example, the treatment of burns, treatment and prevention of scars, for radiotherapy, plastic surgery and cosmetic applications, to protect against UV rays both for medical and non-medical applications, among others. The invention also concerns methods for manufacturing these silicone products The invention further relates a kit comprising a silicone product and an emulsion and/or soap.

BACKGROUND TO THE INVENTION

In the international application BE97/00017 a material is described for medical, paramedical, cosmetic and sport applications. This material includes a silicone layer, disposed on at least one side of an elastic support, that, when applied on the skin, lies in an even manner.

In EP 0251810, a bandage for wounds is described which includes material with apertures, coated with an adhesive silicone gel or a non-adhesive silicone elastomer, or along one side coated with an adhesive silicone gel and along the other side with non-adhesive silicone elastomer. The fibers of support material in this document must be enclosed effectively by the gel so that fabric fibers do not infiltrate in the wound. In addition, the apertures in the material which may be, for example cotton gauze, must not be closed off by the silicone gel.

In U.S. Pat. No. 5,919,476 a bandage is described in the form of a reinforced sheet disposed with silicone-gel for the treatment of scars. The bandage has a first layer of silicone, adapted to adhere to the skin, second layer of a network fabric perforated with multiple apertures, which in contact the first layer and a third layer of silicone. The third layer provides for a non-stick layer that covers the second layer and which allows the bandage to be worn under clothing.

SUMMARY OF THE INVENTION

One embodiment of the present invention is a silicone product comprising a single or double elastic material which is covered along at least one surface with an adhesive or non-adhesive silicone-gel, wherein the elastic material is woven or knitted and comprises polyamide or polyester.

Another embodiment of the present invention is a silicone product as described above, wherein the opposing surface is covered with a non-adhesive silicone gel.

Another embodiment of the present invention is a silicone product as described above, wherein the elastic material is covered along one surface, with an outer cover such that the surface not covered with an over cover is covered with adhesive silicone-gel.

Another embodiment of the present invention is a silicone product as described above wherein the outer cover comprises one or more layers of breathable polyurethane.

Another embodiment of the present invention is a silicone product as described above wherein the outer cover comprises one or more UV protection agents, which provide a UV protection of more than 20 and preferably more than 50 UPF factor.

Another embodiment of the present invention is a silicone product as described above wherein the elastic material comprises at least 57% polyamides.

Another embodiment of the present invention is a silicone product as described above wherein the elastic material has an elasticity of between 135% and 175% in length.

Another embodiment of the present invention is a silicone product as described above where the elastic material is covered with a silicone gel in a quantity of 180 to 250 grams silicone per square meter.

Another embodiment of the present invention is a silicone product as described above where the elastic material comprises at least 81% polyamides Another embodiment of the present invention is a silicone product as described above wherein the elastic material has an elasticity of between 165% and 205%.

Another embodiment of the present invention is a silicone product as described above where the elastic material is covered with a silicone gel in a quantity of 500 to 1500 grams silicone per square meter.

Another embodiment of the present invention is a silicone product as described above which is elastic in one or more directions.

Another embodiment of the present invention is a silicone product as described above where the top cover is moisture permeable.

Another embodiment of the present invention is a silicone product as described above characterised in that the product is washable.

Another embodiment of the present invention is a silicone product as described above characterised that the product is preferably anti-allergic.

Another embodiment of the present invention is a silicone product as described above, wherein the silicon-gel further comprises microcapsules.

Another embodiment of the present invention is a method of making a silicone product as described above comprises the steps of:

obtaining a double elastic material wherein one surface is covered with the outer cover, placing said material, outer cover side down, onto a supporting sheet, placing a moulding means over the non-covered surface of the elastic material and applying silicone paste thereto, optionally removing bubbles, and allowing to set, thereby obtaining a silicone product of the invention.

Another embodiment of the present invention is a method as described above comprising the steps of:

cutting a double elastic material covered with a top cover to the desired size, placing double the elastic material covered with the top cover onto a cardboard sheet with the top cover in contact with the cardboard, placing a framework onto the material and fixing the material and the framework, mixing a silicone paste comprising more than one component and pouring the paste on the material in the framework, optionally removing the framework and transmitting whole assembly of cardboard, elastic material and silicone and paste onto a shaking table where is shaken for at least 1 minute, and allowing the silicone product to set for at least 3 hours, thereby obtaining a product of the invention.

Another embodiment of the present invention is a method as described above where the framework is cardboard framework.

Another embodiment of the present invention is a method as described above, wherein the cardboard framework remains attached during further steps.

Another embodiment of the present invention is a method of making a silicone product as described above comprising the steps of:

coating a paper support with silicone paste,
optionally allowing the paste to partially set,
placing thereover a double elastic material wherein one surface is covered with an outer cover, such that the non-covered surface contacts the paste, and
setting the product, thereby obtaining a silicone product of the invention.

Another embodiment of the present invention is a method of making a silicone product as described above comprising the steps of:

coating a paper support with an adhesive silicone paste,
optionally allowing the paste to partially set,
placing thereover a double elastic material,
optionally allowing the paste to partially set,
coating the opposing surface with non-adhesive silicone paste,
applying an outer cover,
setting the product, thereby obtaining a silicone product of the invention.

Another embodiment of the present invention is a method as described above further including a step cutting the silicone product to size.

Another embodiment of the present invention is a method as described above further including a step of mixing the silicone paste with micro-capsules.

Another embodiment of the present invention is a silicone product as described above method as described above wherein at least one micro-capsules comprise one or more medicaments or compositions.

Another embodiment of the present invention is a silicone product or method as described above where at least one medicament is a skin-treatment medicaments.

Another embodiment of the present invention is a silicone product or method as described above wherein at least one micro-capsules comprises one or more cosmetic products.

Another embodiment of the present invention is a silicone product or method as described above wherein a cosmetic product is a skin cream.

Another embodiment of the present invention is a silicone product obtainable by a method as described above.

Another embodiment of the present invention is a use of the silicone product as described above for treating and preventing scars.

Another embodiment of the present invention is a use of the silicone product as described above in plastic surgery.

Another embodiment of the present invention is a use of the silicone product as described above in radiotherapy.

Another embodiment of the present invention is a use of the silicone product as described above as protection against UV radiation.

Another embodiment of the present invention is a use of the silicone product as described above for making a semi-occlusive bandage.

Another embodiment of the present invention is a use of the silicone product as described above for making a semi-occlusive bandage, able to achieve deeper penetration of applied products such as ointments on the skin.

Another embodiment of the present invention is a use of a silicone product as described above as a therapeutic plaster.

Another embodiment of the present invention is a use of a silicone product as described above as a cosmetic plaster.

Another embodiment of the present invention is a use of a silicone product as described above for making a therapeutic plaster.

Another embodiment of the present invention is a use of a silicone product as described above for making a cosmetic plaster.

Another embodiment of the present invention is a use of a silicone product as described above for the protection of pressure points or friction points on feet and ankles.

Another embodiment of the present invention is a use as described above, wherein said product is comprised in footware.

Another embodiment of the present invention is a kit comprising a silicone product and a container comprising emulsion, said emulsion comprising a base, emulsifiers, active ingredient, optionally glycerine and optionally milk acid and sodium acetate, and optionally anti-microbial agent.

Another embodiment of the present invention is a kit comprising a silicone product and a container comprising soap, wherein said soap comprises aqua, Sodium laureth sulfate, Sodium laureth-11 carboxylate, Sodium hydrochlorate, Laureth-10, Lactic acid, and Sodium lactate.

Another embodiment of the present invention is a kit comprising a silicone product and a container comprising soap and a container comprising emulsion, wherein said soap and emulsion comprise components listed above.

The current invention is related to a silicone product, comprising a double or single elastic material which is disposed with a silicone coating along at least one surface, where the elastic material is woven or knitted, and is made from polyamide, polyester or other elasticated material suitable for weaving or knitting.

In one embodiment of the invention, the elastic material is covered on one surface with protecting polyurethane layer.

In further embodiment, the polyurethane layer of the described silicone product breathes i.e. is permeable to water vapour.

In further embodiment of the invention the silicone products are washable and reusable. According to another aspect of the invention they are preferably anti-allergic.

In preferred embodiment the method includes additional steps where the silicone product is cut to a desired shape.

In preferred embodiment the framework is a plexiglass framework.

In further preferred embodiment the framework is a cardboard framework; consequently cardboard framework does not need be removed in the further steps.

In further preferred embodiment the method includes an additional step where microcapsules are added to the silicone product; preferably these microcapsules are mixed with the silicone gel or paste, or other silicone mixture. These microcapsules may contain a composition which has therapeutic, cosmetic or paramedical applications.

The invention also concerns the use of the described silicone products, and of the silicone products obtained by the methods described, for, among other things, the treatment of skin, for treating and/or prevention of scars, for use in plastic surgery, radiotherapy or cosmetic treatment, as protection against UV rays, for making semi-occlusive treatments.

In further embodiment the invention concerns a silicone product such as that described above, further characterised by the presence of micro-capsules, preferably in the silicone layer, that contain a composition. Preferably these micro-capsules comprise skin healing medicament or substances.

The invention also concerns of above described silicone products for using a therapeutic plaster.

In further embodiment of the invention concerns a silicone product as above described, characterised by the presence of micro-capsules, wherein these micro-capsules contain a cosmetic product, for example skin cream.

The invention, therefore, also concerns above described silicone products for use as a cosmetic plaster.

The invention also concerns the use of above described silicone products for use as paramedical treatment, for example for the protection of pressure points or friction points on feet and ankles or elbows and shoulders, and in footwear or clothing.

DETAILED DESCRIPTION OF THE INVENTION

The present invention relates to silicone products in the form of sheets, dressings, or clothing having an elastic support, covered along one side with an adhesive silicone gel along the other side with a non-adhesive silicone gel. Where the silicone product is not incorporated into clothing or garments, the exposed side, the side which does not come in contact with the skin, may be provided with an outer cover, for example, one or more polyurethane layers. Where is silicone product is incorporated into clothing or garments, said outer cover may be absent. The invention also relates to silicone products which are reusable i.e. washable.

Outer Cover

The repeated use of these silicone products, causes a wear problem, especially along the side which does not come into contact with the skin, i.e. the side exposed to the outside world. Wear can be caused for all kinds of reasons, such as rubbing, if in constant exterior contact with other materials. Moreover, the outer side of the silicone products may clog. Furthermore, the outer side readily blackens with use, especially when worn beneath clothing; it appears unhygienic and is unpleasant or unacceptable to wear. A solution for this problem is the silicone product of the present invention comprising an outer cover to protect against friction. Said outer is disposed along the surface of the product exposed to the outside world, and which does not contact the skin.

The outer cover may also stabilise the silicone coating in the product, preventing it from moving during normal use.

According to another aspect of the invention, the outer cover comprises an ultraviolet (UV) protection function. Such protection allows faster healing and reduces the risk of UV-induced skin cancer, to which scarred and damaged tissue are susceptible. Such damaging UV rays include UV-A and UV-B radiation. According to an aspect of the invention, the UV protection function is by way of an inherent property of the outer cover and/or by additional UV protection) coatings or pigments and/or by providing layers of the cover material (e.g. one or more layers of polyurethane). According to one aspect of the invention, the UV protection factor (UPF) of the outer cover is better than 5, 10, 15, 20, 25, 30, 35, 40, 45, 50, 55, 60, 65, 70, 75, 80, 85, 20, 95 or 100, and is preferably better than 50.

The UV screening function of the outer cover, where appropriate, may selectively admit non-damaging heat radiation.

Heat, in addition to the moisture emitted by the skin, can be utilised by the product to provide therapeutic heat to the skin or scar.

It is an aspect of the invention heat emitted from the body, is reflected under the product, creating an efficient 'greenhouse' effect of warming beneath the product, creating a moisture environment.

In Table 1 the ultraviolet protection factors (UPF) are reproduced for socks, made in several materials by several producers, in an unstretched, relaxed state. For the silicone products the UPF only in the relaxed state are given.

TABLE 1

UPF values of for sock garments is relaxed in or stretched states, relaxed state only for the silicone products.

| Reference | UPF in relaxed state | UPF in stretched state |
|---|---|---|
| Woven socks | | |
| Tricolast ® | >1000 | 237 ± 12 |
| Juzo ® | >1000 | 136 ± 12 |
| Thuasnes ® | >1000 | 76 ± 3 |
| Maynat ® | >1000 | 120 ± 5 |
| Machine made net-socks | | |
| Anvarex ® | 4.8 ± 0.1 | 4.1 ± 0.1 |
| Cereplas ® | 5.6 ± 0.1 | 4.5 ± 0.1 |
| Jobst ® | 6.1 ± 0.2 | 4.7 ± 0.1 |
| Lymed ® | >1000 | 199 ± 19 |
| Silicone products | | |
| TGSe ® | 14.2 ± 0.4 | — |
| TGSe L ® | 12.1 ± 0.5 | — |
| TES ® | 16.5 ± 1.1 | — |
| Cica-care ® | 1.1 ± 0.1 | — |

Figure 1:
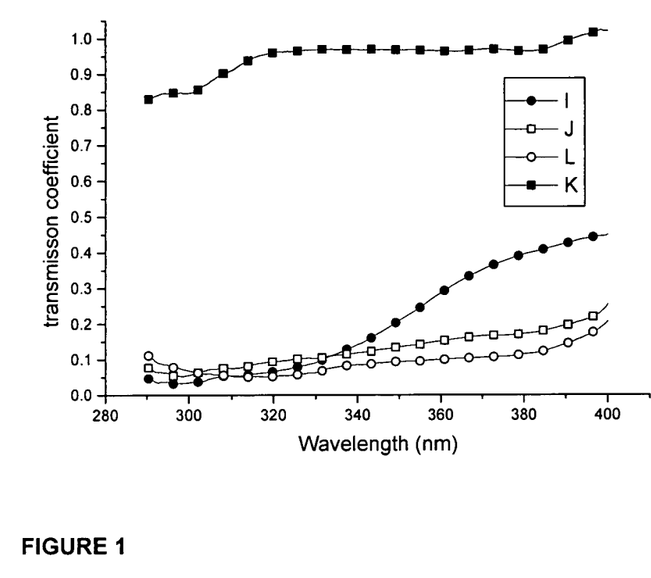
FIG. 1: UV-transmission data at different wavelengths for several silicone the products wherein L=TES (corresponds to ScarBan® MTM of the present invention), I=Scarflex, J=Scartlex Light K=Cica-Care®.

In FIG. 1 UV-transmission data for several silicone the products in several materials by several products, is shown. Such as can be inferred, the silicone products of the invention (L=TES corresponding to ScarBan® MTM) give by far the best results. Furthermore, the characteristics of the following elements are shown: Scarflex (also known as Scarban® elastic) (indicated in the legend with I), Scarflex Light (also known as Scarban® Light) (indicated in the legend indicated with J) and Cica-Care® (indicated in the legend with K).

According to another aspect of the invention, the outer cover is waterproof. According to another aspect of the invention, the outer cover also allows the skin beneath to breath (i.e. is moisture permeable). Suitable outer covers according to the invention are made from one or more layers of polyurethane).

The outer cover may be provided with colorings, logos, pictures, drawings or any other type of marking. Such markings may act, for example, to personalise the silicone product, or as an indication of the product in use. In the case of children, cartoons may be provided thereon which will help to increase the psychological state of mind of the patient. The outer cover may be provided in a color to match the color of the skin of the subject. The outer cover may further be provided in different textures Tests have shown that a durable silicone sheet may also be elastic in the present invention. Specific knitted or woven materials may be used in the current invention as elastic support onto which the silicone coating is deposited, so making durable silicone sheets and products. This product contrasts with known products, having non-woven supports.

According to an aspect of the invention, the silicone product, excluding outer cover, is 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3 mm thick, or greater than 3 mm thick, preferably 1.2 mm thick.

The silicone products of the invention are obtained by given combinations of the elastic material, made from woven or knitted material, and the specific composition of the silicone coating have particular properties. By a combination of elastic material and silicone, a silicone product is obtained that is particularly durable, in contrast to known silicone products, which are very delicate. For example, for the ScarBan® Elastic (see Examples) a life span of at least 2 months is found, and for the ScarBan® Light (see Examples) a lifespan of at least 1 month is found.

Moreover, according to an embodiment this elastic material may be covered with the protecting outer cover as a result of which these products obtain additional waterproofness.

Moreover, the silicone products of the invention are preferably anti-allergic, and have preferably excellent moisture-permeability (i.e. are able to breath). They also have the possibility to be dirt repelling, by virtue of the polyurethane layer.

According to one embodiment of the invention, given configurations of the silicone products are able to be also washed, therefore, they are reusable. During the wash process the silicone may lose its adhesiveness, but it returns after drying.

Silicone Product Washing Substance

Another embodiment of the invention is a silicone product of the invention provided with a washing substance. Such combination may be packaged as a kit. The washing substance has the property that is capable of removing grease from the silicone product, without damaging the silicone layer. Such washing substances are known in art and include soap, detergent, non-ionic detergent. One aspect of the invention is a kit comprising one or more silicone products as described herein and one or more bars of soap. One aspect of the invention is a kit comprising one or more silicone products as described herein and one or more containers, tubes or vials of soap.

According to an aspect of the invention, a soap comprises aqua, Sodium laureth sulfate, Sodium laureth-11 carboxylate, Sodium hydrochlorate, Laureth-10, Lactic acid, Sodium lactate. Such ingredients may be formulated into soap according to known methods.

The properties of sodium lauryl ether sulfate are a anionic surfactant, good cleaning properties and foam shaping and is gentle on the skin.

The properties of sodium laureth-11 carboxylate+laureth-10 are very good cleaning properties, very mild for the skin and the eyes, good foaming and stability improve Elastic Material In a preferred embodiment the silicone product of the invention is made covering an elastic material, such as, for example, polyamide, polyester having a breathable polyurethane coating.

In one embodiment, the silicone product according to the invention comprises an elastic material which is 57% to 81%, 60% to 77%, 65% to 75%, 67% to 73%, 69% to 71% polyamide, and the product has an elasticity of, between 135% and 205%, 140 to 200, 150 to 190, 160 to 180, 165 to 175% in length. Preferably is the elastic material is covered with a silicone coating in an amount between 180 to 1500, 200 to 1400, 300 to 1300, 400 to 1200, 500 to 1100, 600 to 1000, 700 to 900, 750 to 850 grams per square meter.

In one embodiment, the silicone product according to the invention comprises an elastic material which is 57% polyamide and 43% elastane (WN562), and the product has an elasticity of between 135% and 175% in length and elasticity of between 150% and 190% in width. Preferably the elastic material is covered with a silicone coating in an amount between 180 to 300 grams per square meter.

Preferably the pressure garments has a elasticity between 80% and 100% in the length and width. A preferred example has a composition of polyamide 77% and elastomer 23%

Preferably the silicone product of the invention comprises an elastic material which is 81% polyamides and 19% elastane, and the product has an elasticity between 165% and 205% in length and between 80% to 100% in width. Preferably the elastic material is covered with a silicone coating in an amount of 500 to 1500 grams per square meter.

Tissue for the uv products is a compilation of 90% promodal (modal 63%+lyocell 27%) and 10% elastane. The elasticity in the length is between 75% and 95% and in the width between 100% and 130%. The weight is about 210 $gr/m^2$.

A preferred example is waterproof breathable tissue composed of polyester knitted fabric (62%) with a breathable polyurethane layer (38%) having an elongation of 15 (long) and 240 across (as measured by ISO13934-1).

According to one aspect of the invention, the product has elasticity only in one direction. e.g. in the direction of the length of the product, or in the direction of the width, in one directly across the plane of the product. According to another aspect of the invention, the silicone product has elasticity in two directions e.g. in the direction of both the length of the product, and in the width thereto. The elasticity in the width and length may be the same or different According to an aspect of the invention, the silicone product has an elasticity in one or more given directions (e.g. length, breadth). Such directions may depend, for example, on the base elasticity of the elastic material.

According to an aspect of the invention, the silicone product has a region of greater or lesser elasticity in at least part of the product, depending on the elasticity and the weave of the threads in said part of the elastic material. Such embodiments allows greater expansion, for example, in the centre of the silicone product.

The use of woven or knitted elastic materials gives the additional advantage of an extremely good protection against UV radiation. This is in comparison with conventional dressing products, for example, Juzo®, Thuasnes®, Anvarex®, Maynat®, Cereplas®, Jobst®, Lymed®, Cica-care® which do not exhibit such protection. Comparison studies have shown that ScarBan® product (see Table 1) by far has the lowest UV transmission factor and the highest ultraviolet protection factor (UPF). Such UV protection offer the advantages of reduced risk against skin cancer and faster healing times. According to an aspect of the invention, the UV protection function is by way of an inherent property of the elastic material and/or by additional UV protection coatings or pigments and/or by providing layers of the elastic material. According to one aspect of the invention, the UV protection factor (UPF) of the elastic material is better than 5, 10, 15, 20, 25, 30, 35, 40, 45, 50, 55, 60, 65, 70, 75, 80, 85, 20, 95 or 100, and is preferably better than 50.

The elastic property of the silicone product also provides an advantage that a tension is applied across the scar tissue. The inventors have found that a tension supplied by the product creates a sustaining pressure which improves the healing process. Such tension may be made directional with the use of a silicone product stretchable in a single direction only (e.g.

lengthways). This effect of the applied tension, combined with the 'greenhouse' effect of the product, further enhances the healing property. Such effect is especially apparent when the product is applied to tubular skin areas e.g. the limbs, neck.

Silicone Gel

According to an embedment of the invention, a silicone gel is one known the art of scar and treatments, and is described elsewhere (e.g. EP 0 251 810, WO 02/45698). Specific examples of silicone paste are provided in the Examples section below.

According to one embodiment of the invention, the silicone gel forms a coating that does not permeate the fabric. This may be achieved by the elastic material chosen and the way silicone layers are coated. For example, the number of threads in both directions of the elastic material may be such that openings are a maximum of 0.1 $mm^2$ in size, and preferentially a maximum of 0.05 $mm^2$ in size. The silicone layers, and especially the adhesive silicone layer may set to such an extent, that it does not penetrate in the fabric.

Backing Layer

In one embodiment of the invention, the silicone product comprises a backing layer which is removed before application to the subject. The backing layer reversibly adheres to the silicone layer intended for contact with the skin of the subject. The backing layer may be made of any suitable material such as, for example, polyethylene, polythene or other polymeric substance. According to an aspect of the invention, the backing layer is smooth, or is regularly patterned with pits or grooves. Such patterns enable easy removal and reapplication of the silicone product. An example of such pattern is a diamond structure. It is an advantage that the reusable silicone product adheres reversibly to the backing layer to provide storage between periods of use.

According to one aspect of the invention, the backing layer comprises a series of indented pits, arranged in diamond formations. Each pit provide an air gap when the silicone layer is adhered thereto. The diamond arrangement and air gap facilitates the ease of removal of the silicone layer, so prolonging the life span during use.

Shapes and Incorporation into Garments

According to one embodiment of the invention, the silicone product is covered along at least one side with a silicone coating of varied composition and cross-section. The different cross-sections, shapes, and possibilities of the silicone products comply with the requirement of different parts of the body. Examples of various shapes of product are provided is FIG. 4. One silicone product may be used for several types of skin, scars; and/if suitable skin types are available, then another silicone product may be used. Examples of cross-sections include tubular for application to a limb.

Where the silicone product is incorporated into garments, materials for such garment are any which have properties suitable for wearing. Properties include one or more of comfort, low/non-allergic, washability, low-shrinkage, elasticity. Examples of suitable materials include fabrics composed of polyamide and polyester.

According to an aspect of the invention, a silicone product incorporated into a garment does not comprise an adhesive silicone layer. Such silicone products are prepared as mentioned herein, wherein the silicone paste or gel is non-adhesive. Such products may be coated on one or both sides with non-adhesive silicone.

According to another aspect of the invention, a silicone product incorporated into a garment does not comprise an outer cover.

According to an aspect of the invention, the silicone product is made into at least part of a garment which can be worn by a subject. Such garments are for example suitable for hands, arms, legs, chest, or other parts of the body and may include gloves, mittens, socks, t-shirts, stockings and limb-bands. According to an aspect of the invention, a garment is close fitting. According to another aspect of the invention it is made to measure. The silicone layer may be disposed across the entire skin-contacting surface of the product, or it may be disposed in one or more regions, corresponding to at least the regions of the scar.

Described silicone products can, therefore, adopt several forms and be prepared in several manners dependent on the desired application.

Method of Manufacture

The invention also relates to a method for making silicone products. According to an aspect of the invention, a method of making a silicone product comprises the steps of:

obtaining a double elastic material wherein one surface is covered with an outer cover, laying said material, outer cover side down, onto a supporting sheet, placing a moulding means over the non-covered surface of the elastic material and applying silicone paste or gel thereto, optionally removing bubbles, and allowing to set, thereby obtaining a silicone product of the invention The moulding means is any means of containing the silicone paste or gel over the elastic material in a shape comprising at least the desired silicone product. Such means includes a mould, a solid sheet (e.g. made of cardboard, polypropylene) having several apertures each corresponding to a shape of the product, a framework of criss-crossing rafters which define a series of apertures. The depth of the moulding means may correspond to the desired thickness of the silicone coating.

According to an aspect of the invention, a method of making a silicone product comprises the steps of:

cutting a double elastic material covered with a outer cover to the desired size, placing double the elastic material covered with the outer cover onto a cardboard sheet with the outer cover in contact with the cardboard, placing a framework onto the material and fixing the material and the framework, mixing a silicone paste or gel comprising more than one component and pouring the paste or gel on the material in the framework, optionally removing the framework and transmitting whole assembly of cardboard, elastic material and silicone and paste or gel onto a shaking table where is shaken for at least 1 minute, and allowing the silicone product to set for at least 3 hours.

According to an embodiment of the invention, the new silicone products or sheets are manufactured in a following generally described manner (for example in a silicone station).

Firstly, the elastic material, which is generally available on a roll, is cut into sheets of approximately 50 cm by 50 cm or other size, depending on the application. Cut sheets have 2 different sides (surfaces). It is the side which is to be covered with the polyurethane layer that is placed downwards in contact with a cardboard sheet, and which is then placed onto a coating tablet.

Then a framework is laid over the elastic material. According to one embodiment of the invention, a plexiglass framework, 1.7 mm thick, is laid over the elastic material, and this whole assembly is fixed under the criss-cross arrangement of rafters. In one embodiment a hydraulic system is used to apply pressure.

Once correctly arranged (no tension, wrinkles or warps in the elastic material) the silicone paste is prepared. According to one embodiment, the silicone paste comprises a mix of the a) & b) silicone components according to a certain formula (described below, for example, in Example 1). According to one embodiment of the invention the total silicone paste is in the range of 10 to 400, 50 to 350, 100 to 300, 150 to 250 and preferably 280 grams. However, this quantity is among other factors dependent on, for example, the desired cross-section of the silicone layer and can, according to the aimed at application, be modified. The paste is then poured out and spread in the framework, principally on the elastic material.

A spatula or squeegee which one may install on the coating tablet is used to spread the paste evenly within the framework, ensuring that the corners are sufficiently filled. As soon as the quantity of paste appears proportionally divided within the framework, the elastic material and silicone paste may be slid onto a separate plate to be then brought to a device for removing bubbles. Such device may be any of the art, and includes a shaking table. Where a shaking table is employed, it is used for approximately one minute to remove bubbles efficiently from the silicone. This assembly is then allowed to set for a minimum of 3 hours.

During that period quality control checks may be employed, where attention is paid especially to bubbles, substance particles, and other imperfections. If irregularities are present, they may be seen and the assembly is not further used. This way the quality of the end product is assured.

According to an embodiment of the invention, the quality control of the adhesiveness may be exercised manually by pressing, and feeling the framework of the plate with the thumb. By this way, adhesiveness of the surface can be approved. After the quality control (adhesive strength and irregularities) the plates are covered with polythelene foil backing layer.

One embodiment of the method include the use of a cardboard sheet as a framework. This has the advantage that it does not have be detached as the entire assembly can be sent to a cutting machine.

Then the desired silicone products are cut out from sheets. This is possible by using, for example, a manual cutting table, an automatic cutting table, or using a laser cutter. Alternatively, the desired form is punched out from sheets.

According to an aspect of the invention, a method of making a silicone product comprises the steps of:
coating a paper support with silicone paste,
optionally allowing the paste to partially set,
placing thereover a single elastic material wherein one surface is covered with an outer cover, such that the non-covered surface contacts the paste, and
setting the product, thereby obtaining a silicone product of the invention.

According to one embodiment, the silicone paste comprises a mix of the a) & b) silicone components according to a certain formula (described below, for example, in Examples 1 and 2). According to one embodiment of the invention the total silicone paste is in the range of 10 to 400, 50 to 350, 100 to 300, 150 to 250 and preferably 180 grams per square meter.

However, this quantity is among other factors dependent on, for example, the desired cross-section of the silicone layer and can, according to the aimed at application, be modified. Such method is described in detail in Examples 1 and 2, one or more elements of which may be applied to the above embodiment.

According to an aspect of the invention, a method of making a silicone product comprises the steps of:
coating a paper support with an adhesive silicone paste,
optionally allowing the paste to partially set,
placing thereover a single elastic material,
optionally allowing the paste to partially set,
coating the opposing surface with non-adhesive silicone paste,
applying an outer cover
setting the product, thereby obtaining a silicone product of the invention.

According to one embodiment, the silicone paste comprises a mix of the a) & b) silicone components according to a certain formula (described below, for example, in Examples 3 and 4). According to one embodiment of the invention the total adhesive silicone paste is in the range of 100 to 800, 200 to 700, 300 to 600, 400 to 500 and preferably 180 grams per square meter. According to another embodiment of the invention the total non-adhesive silicone paste is in the range of 100 to 600, 200 to 500, 300 to 400, 500 and preferably 340 grams per square meter. However, these quantity is among other factors dependent on, for example, the desired cross-section of the silicone layer and can, according to the aimed at application, be modified. Such method is described in detail in Examples 3 and 4, one or more elements of which may be applied to the above embodiment.

Of course, the described method above is only one example, and the person skilled in the art can adapt these embodiment further according to their needs and desired applications.

Carrier for Other Substances

According to one aspect of the invention, a silicone product is a carrier for the delivery or supply of a composition. Such composition may be any suitable to enhance the treatment. It may comprise, for example, one or more substances which assist in the prevention of scars, for the treatment of burns, for the treatment of infections, for relieving pain. A composition may comprise, for example, moisturizing cream, aloe-vera-containing cream, vitamin E formulations or combinations thereof. Composition may be present on the surface or in pits or grooves formed in the silicone. Alternatively, the composition may be present in microcapsules which are present in the silicone.

In one embodiment of the invention, the silicone is mixed with microcapsules before coating onto polyamide material.

The invention concerns combination also all possibilities of above described separate components of the silicone products, such as for example:
a thin silicone plaster which offers certain occlusiveness,
microcapsules that are held in the silicone layer which release substances deep into the covered parts,
protection of feet or legs or certain pressure points or friction areas.

Emulsion

According to another aspect of the invention, an emulsion is applied to the scar or skin prior to the application of the silicone product, and/or after the removal of the silicone product. Such emulsion may comprise a composition as mentioned above, and have a therapeutic or cosmetic effect.

Furthermore, said emulsion may comprise components, which provide one or more of the following properties:
make putting pressure clothing on easier,
reduce bacterial growth,
reduce itchiness,
provide a hydrating and softening effect.

One aspect of the Invention, the emulsion comprises hydrating agent and optionally barrier agent. With respect to hydration, the new formed skin is very dry and sensitive. An emulsion comprising hydrating agent and barrier agent, rehydrates the skin and reduced moisture loss therefrom. The healed skin is smoother. Furthermore, a well hydrated epidermis reduces scarring. Where the epidermis has not started to be repaired, collagen in the scarring tissue can be reduced by the application of the emulsion The barrier agent reduces water loss, more specifically reduces trans-epidermal water loss (TEWL). An increase of the TEWL the indicates is unfavourable, and is accompanied by raised release of keratinosomen in the stratum granulosum of the epidermis. The keratinosomen is involved in the production of lipids for "intercellular cement" in order to form a protective water repellent film.

accelerated, spontaneous production of keratinocytes

The formation of the water-repellant film often results in a bulge of the epidermis. The consequence is the formation of a harsh stratum, dryness, flaking skin. The increased TEWL also causes a feeling of stretching of the skin, and need to scratch, leading to the release of more keratinisomen and cell production, so exacerbating the problem.

According to one aspect of the invention, the emulsion comprises anti-itching agent. Itching is problem at the site of repaired skin. Scratching damages the repaired area.

According to one aspect of the invention, the emulsion comprises a base, dispersant (emulsifiers), active ingredient, optionally glycerine and optionally milk acid and sodium acetate, and optionally anti-microbial agent. Properties and examples of such components are provided below:

Base

According to an aspect of the invention, the base comprises dimethicone.

These liquid silicone oils are tolerated by the skin and show no or little interaction with the silicone product. These stable silicone oils spread well, do not feel greasy, they are semi-occlusive and feel gentle and silky against the skin.

The emulsion spreads out well, because of this one does not need to apply much emulsion to the silicone product or to the skin.

According to one aspect of the invention, polydimethylsiloxane is used as a base. It is environmentally sound, exhibits no apparent toxicological effects, is non-irritating and is low/no sensitising properties.

Emulsifier (Dispersant)

According to the one aspect of the present invention, an emulsifier is a non-ionic emulsifying agent, suitable for skin appliance. Such are known in the art. According to an aspect of the invention, an emulsifier has a pH between 5 and 6.

According to one aspect of the invention, an emulsifier is Steareth-2 (CAS: 9005-00-9), or Polyoxyethylene (2) stearyl ether.

According to one aspect of the invention, an emulsifier is Steareth-9.

According to another aspect of the invention, an emulsifier is Steareth-21 (CAS: 009005-00-9) or Polyoxyethylene (21) stearyl ether.

Active Ingredient

According to one aspect of the invention, an active ingredient is an agent which reduces the feeling of itchiness. Itchiness, if relieved by scratching, can damage newly repaired skin. According to an aspect of the invention, an anti-itchiness agent is laureth-9.

It is also known as polidocanol or hydroxypolyethoxydodecane Laureth-9 topical anathetic gives a local anaesthesia effect. This impact is used in moderating products to reduce the tingling.

Glycerine

According to another aspect of the invention, an emulsion comprises glycerine.

The amounts and usage of glycine are known in the art.

Glycerine controls the hydrating effect of the emulsion. It improves skin flexibility. Recent studies have shown the combined impact of an improvement of the hydration stabilised barrier effect using glycerine. Both properties occur independently of each other and have been proved scientifically: glycerine creates a stimulus for barrier convalescence and improves the hydration of the stratum corneum, even up to 7 days after finishing treatment. Furthermore, glycine is not irritating to the skin.

Milk Acid and Sodium Lactate

These raw materials are natural products, obtained by fermentation of sugar according to an aspect of the invention, they are a component of the emulsion. They are natural components of the skin with hydrating properties. Milk acid raises cellular turn-over of the Stratum Corneum. Usage of milk acid and sodium lactate is known in the art. The use of milk acid also has anti-microbial action (see below).

Anti-Microbial Compounds

The silicone product may also comprise one or more antibacterial agents, suitable for contact with the skin. As microorganisms grow well in warm wet surroundings of the product applied to the skin, the product could ready emit an unpleasant odor. The low pH and the anti-microbial properties of milk acid form an unfavourable environment for micro-organisms and so reduces the embarrassing odors which may arise from the product.

Uses

Another embodiment of the present invention is a use of a silicone product for the treatment of skin and prevention of scars.

The silicone products of the invention are characterised in particular, by their specific composition; they give an extremely good protection against UV rays.

The silicone products of the inventions may be employed in the treatment of scars, plastic surgery and all other applications within the care environment. Further applications possible are radiotherapy, making up a semi-occlusive to almost 100% occlusive dressings, the use as protection against UV rays, etc.

Most of these applications have the advantage that scars of all kinds are reduced or are avoided through the use of the silicone products of the invention.

A specific application for the silicone products is the treatment and the prevention of hypertrophic and keloid scars.

There are also related markets for the silicone products which find interesting applications, and also applications such as radiotherapy, traumatology, lymph drainage, semi-occlusive dressing applications and several dermatological applications.

For example the silicone products also have possibilities in the cosmetic and paramedical sector. The occlusive property of the product which is provided by the silicone products, allows administered skin creams to achieve deeper penetration with a smaller quantity material. Consequently, the effectiveness of the creams is enhanced.

The silicone product can also be used in the care of the feet and for the protection of pressure points in shoes (diabetic foot, etc. . . . )

The silicone product of the invention may be applied at regular intervals. For example, an initial application of 1 hour per day, may be subsequently followed by constant or increased durations of wear time. It is an aspect of the invention, that the product is worn every day, and the duration of wear is increased until it is worn for 15, 16, 17, 18, 19, 20, 21, 22, 23 or 24 hours a day.

The silicone products are fabricated from several compositions of elastic material and silicone coating. Below a number of these silicone products have been described products in more detail, as well as embodiments of methods for their fabrication. The invention described below is not limited to the Examples.

Machines for Fabrication

Another embodiment of the invention also concerns machines for the fabrication of the silicone products. These machines may be provided with a heating element and are simplified versions of coating machines which are already known. For making the ScarBan® Elastic products, for example, a machine was automated to become a semi-automatic silicone station.

DETAILED DESCRIPTION OF THE FIGURES

FIG. 1: UV-transmission data for several silicone the products in several materials by several products is shown. The silicone products of the invention (L=TES® corresponding to ScarBanMTM) give the best results. The characteristics of the following elements are shown: Scarflex® (I), Scarflex Light® (J) and Cica-Care® (K). The X-axis is the wave length, expressed in nanometer. The Y-axis is the transmission coefficient.

Figure 2:
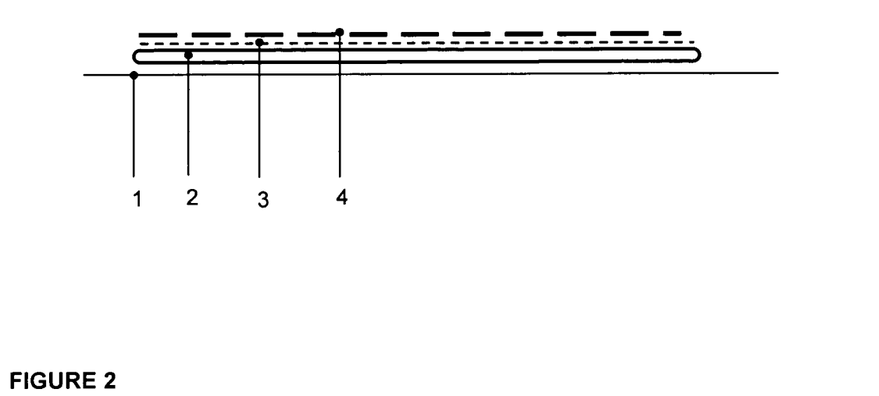
FIGS. 2 and 3: Exploded views of a transverse cross-sections of silicone products according to the invention.

FIG. 2: Exploded view of a silicone product of the present invention. Shown is a backing layer (1), an adhesive silicone layer (2), an elastic fabric (3), and a outer cover (4).

Figure 3:
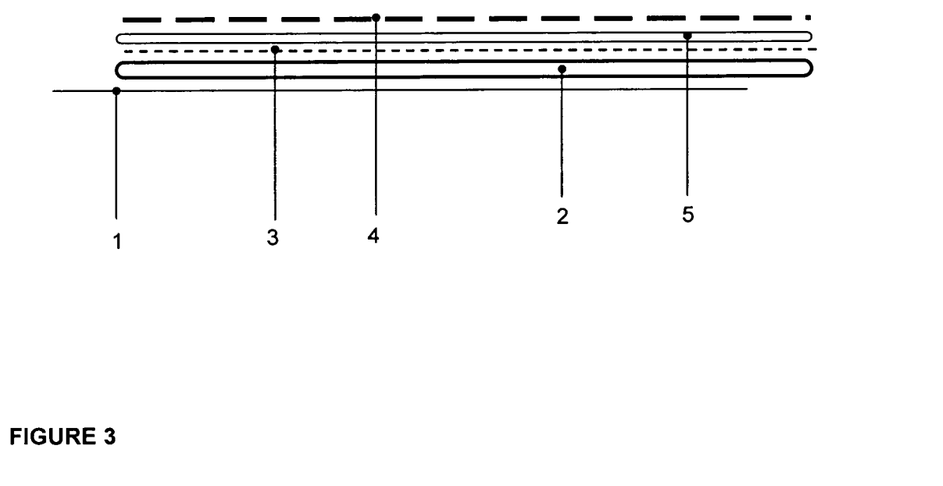

FIG. 3: Exploded view of a silicone product of the present invention. Shown is a backing layer (1), an adhesive silicone layer (2), a non-adhesive silicone layer (5) an elastic fabric (3), and a outer cover (4).

Figure 4:
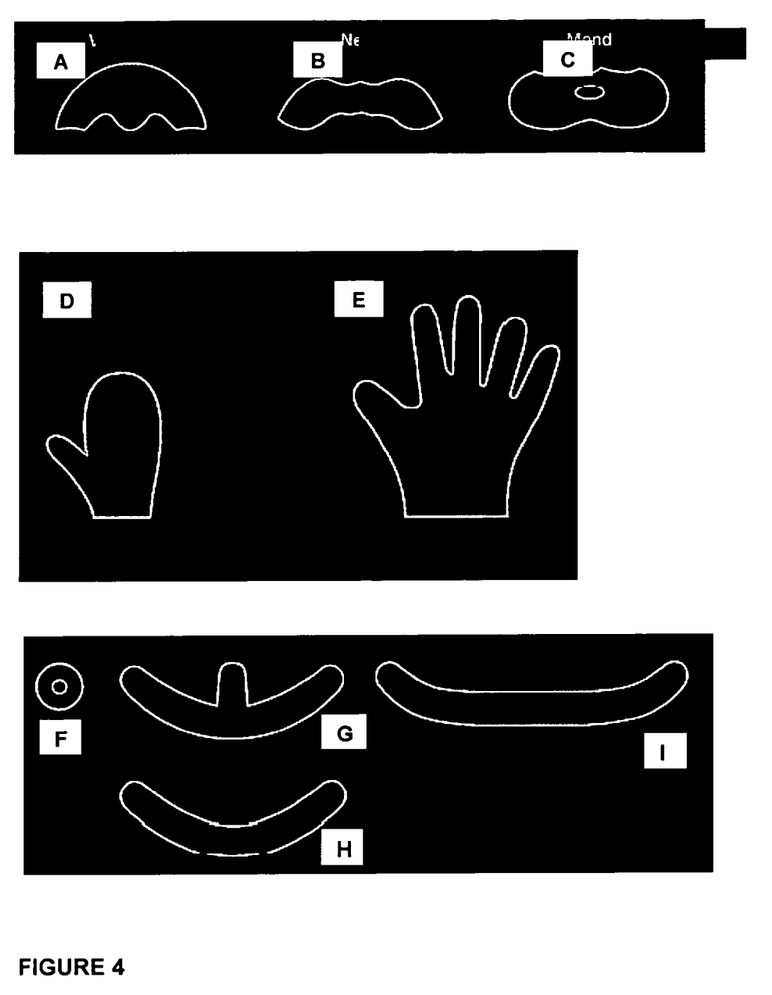
FIG. 4: Examples of shapes of product (A to H) according to the invention.

FIG. 4: Shapes of product according to the invention: A—suitable for application to the forehead, B—suitable application to the nose, C—suitable for application to the mouth, D—suitable for application to the hand (especially of a child), E—suitable for application to the hand (especially of an adult), F—suitable for application to the nipple, G—suitable for application to the abdomen before or after pregnancy, H—suitable for application to the abdomen before or after pregnancy, I—suitable for application to abdomen.

EXAMPLES

The new silicone products according to the invention are known under the trademark ScarBan®. The ScarBan® products are also indicated in this invention under the following trademarks: Tricolast®, TGSe® (corresponds to ScarBan® Elastic), TGS Light® (corresponds to ScarBan® Light) and TES (corresponds to ScarBan® MTM). In the below these silicone products are described with their trademark name.

1. ScarBan® Light

In this Example, the ScarBan® Light silicone product is made from a thin single elastic polyester material, covered with medical adhesive silicone along the one side and protective polyurethane layer along the other side.

The basis material is an elastic polyester

A preferred example is waterproof breathable tissue composed of polyester knitted fabric (62%) with a breathable polyurethane layer (38%) having an elongation of 15 (long) and 240 across (as measured by ISO13934-1.

The fluid product (silicone or polyurethane) is applied on a paper support.

The partly set layers are put in contact with the elastic material and the whole assembly is guided through a furnace for further setting, to reach the desired crosslinking of the silicone or PU coating.

2. ScarBan® Elastic

These are generally made from a 1.2 to 3 mm thick medical adhesive silicone layer, fixed onto double elastic material. This corresponds to 1500 grams of silicone by square meter.

The elastic material comprises 81% polyamides and 19% elastane, of 105 grams (±10%) per square meter, with an elasticity between 165% and 205% in length, preferably 185%, and an elasticity between 80% and 100% in breath, preferably 90%. The material has 60 stitches per cm in the one direction and 31 wales per cm in the other direction. The elastic polyamide is covered with protecting polyurethane layer. These silicone products are preferably made in sheets with a useful surface area of 40 by 45 cm.

3. ScarBan® Roller Dressing

This is a slightly adhesive silicone bandage which is made from a double elastic polyamide or polyester material which is covered along both sides or one side (surface) with silicone; on the one hand with adhesive silicone gel and on the other side with non-adhesive silicone.

Temporary paper supports are placed on the coating station for deposition of a low sticking silicone or breathable PU coating. Several coating techniques can be used: knife coating, roller coating, calander coating, etc.

The fluid product (silicone or polyurethane) is applied on a paper support.

The partly set layers are put in contact with the elastic material and the whole assembly is guided through a furnace for further setting, to reach the desired crosslinking of the silicone or PU coating.

In a further stadia, the non coated side of this material is coated with the silicone gel. Again there are several coating techniques possible.

The coated complex is again guided through a furnace for further setting, to reach the desired crosslinking of the silicone gel.

Once the product is made, several sizes can be manufactured, depending on the parts of the body intended for treatment. Preferably packaging is adapted so that its has several functions such as advertising or ease of storage. Packing containing the cleaning instructions plays a role in the lifespan of the product. The patients will use the product, and with different periods between reuse, the patients will take the product away with them. For this reason there is a need to a packing which allows the patient to keep the product in a safe manner.

4. ScarBan® MTM

This was made from a double elastic polyamide material which is coated with non-adhesive silicone, as above described, and then made into garments, or requested tailored made products.

For the non-stick coating, a mixture was made of commercially available components for a silicone polyadditive product. The first component, known as part (a), a mixture of polymethylvinyl includes, polymethylhydrogenosiloxanes and silica was mixed thoroughly at room temperature in a proportion of 100/10 by weight with a second component, known as part (b), that included was a mixture of polymethylvinylsiloxanes, silica and platinum.

Liquid (a) has a viscosity at 25° C. of 40,000 mPa whereas liquid (b) has a viscosity at 25° C. of 20,000 mPa. After mixing the fluid was degased by the application of vacuum of approximately 30 to 50 mbar. Setting was initiated at room temperature as from the moment the components were mixed.

The mixture was coated such that the density of silicone along the free side of elastic polyamide material was 250 g per square meter. The mixture was allowed to set. The temporary support was removed. The elasticity in the length direction of the composite product was 75%.

The basis material was an elastic polyamide with the same composition such as described for WN562 above. The non-adhesive silicone coating is introduced in a proportion of 250 grams per square meter.

An elastic material has 57% polyamide and 43% elastane, and the product has an elasticity of between 135% and 175% in length and elasticity of between 150% and 190% in width. Preferably the elastic material is covered with a silicone coating in an amount between 180 to 300 grams per square meter.

This silicone product is especially used to make tailor-made silicone attire, such as clothing, gloves, etc. By means of a pattern which is drawn manually and is cut, one can provide all parts of the body with silicone. In one embodiment, a tailor-made fitting uses a CAD system and automatic cutting table to cut out the patterns.

Several techniques are used to put the separate pieces together such as welding, melting, stitching, . . . etc.

What is claimed is:

1. A silicone product comprising a single or double elastic material which is covered along only one surface with an adhesive or non-adhesive gel consisting of silicone, and along only the other surface with an outer cover of one or more layers of breathable polyurethane, wherein the elastic material is woven or knitted and comprises polyamide or polyester and is covered with said silicone in an amount of 500 to 1500 grams per square meter.

2. The silicone product according to claim 1 wherein the outer cover comprises one or more UV protection agents, which provide a UV protection of more than 20 UPF factor.

3. The silicone product according to claim 1 where the elastic material comprises at least 57% polyamides by weight.

4. The silicone product according to claim 3 wherein the elastic material has an elasticity of between 135% and 175% in length.

5. The silicone product according to claim 1 where the elastic material comprises at least 81% polyamides by weight.

6. The silicone product according to claim 5 wherein the elastic material has an elasticity of between 165% and 205% in length.

7. The silicone product according to claim 1 which is elastic in one or more directions.

8. The silicone product according to claim 1 where the top cover is moisture permeable.

9. The silicone product according to claim 1 characterized in that the product is washable.

10. The silicone product according to claim 1 characterized in that the product is anti-allergic.

11. The silicone product according to claim 1, wherein the silicone-gel further comprises microcapsules consisting of a medicament or cosmetic product.

12. A method of making a silicone product of claim 1 which comprises the steps of:
    obtaining a double elastic material wherein one surface is covered with an outer cover,
    placing said material, outer cover side down, onto a supporting sheet,
    placing a molding means over the non-covered surface of the elastic material and applying silicone paste thereto, optionally removing bubbles, and
    allowing to set, thereby obtaining a silicone product of the invention.

13. The method according to claim 12 comprising the steps of:
    cutting the double elastic material covered with a top cover to the desired size,
    placing double the elastic material covered with the top cover onto a cardboard sheet with the top cover in contact with the cardboard,
    placing a framework onto the material and fixing the material and the framework,
    pouring the paste on the material in the framework,
    optionally removing the framework and transmitting the whole assembly of cardboard, elastic material and silicone paste onto a shaking table and shaking for at least 1 minute, and
    allowing the silicone product to set for at least 3 hours, thereby obtaining a product of the invention.

14. The method according to claim 13 where the framework is a cardboard framework.

15. The method according to claim 14, wherein the cardboard framework remains attached during further steps.

16. A method of making a silicone product of claim 1 comprising the steps of:
    coating a paper support with silicone paste,
    optionally allowing the paste to partially set,
    placing thereover a double elastic material wherein one surface is covered with an outer cover, such that the non-covered surface contacts the paste, and
    setting the product, thereby obtaining a silicone product of the invention.

17. A method of making a silicone product of claim 1 comprising the steps of:
    coating a paper support with an adhesive silicone paste,
    optionally allowing the paste to partially set,
    placing thereover a double elastic material,
    optionally allowing the paste to partially set,
    coating the opposing surface with non-adhesive silicone paste,
    applying an outer cover, and
    setting the product, thereby obtaining a silicone product of the invention.

18. The method according to claim 13 further comprising a step of cutting the silicone product to size.

19. The method according to claim 13 further comprising a step of mixing the silicone paste with micro-capsules consisting of a medicament or cosmetic product.

20. The silicone product according to claim 11 where the medicament is a skin-healing medicament.

21. The silicone product according to claim 11 wherein the cosmetic product is a skin cream.

22. A silicone product obtainable by a method according to claim 12.

23. A method for the treatment of burns which comprises administering the silicone product according to claim 1 to a patient in need thereof.

24. A method for treating and preventing scars which comprises administering the silicone product according to claim 1 to an individual in need thereof.

25. A method of protecting against UV radiation which comprises covering skin with a material comprising the silicone product according to claim 1.

26. A semi-occlusive bandage, able to achieve deeper penetration of applied products such as ointments on the skin comprising the silicone product according to claim 1.

27. A therapeutic plaster comprising the silicone product according to claim 1.

28. A cosmetic plaster comprising the silicone product according to claim 1.

29. A method for the protection of pressure points or friction points on feet and ankles which comprises administering the silicone product according to claim 1 to the pressure point or friction point in need of treatment.

30. The method according to claim 29, wherein said product is comprised in footwear.

31. The silicone product according to claim 1 wherein the outer cover comprises one or more UV protection agents, which provide a UV protection of more than 50 UPF factor.

32. The method according to claim 19 where the medicament is a skin-healing medicament.

33. The method according to claim 19 wherein the cosmetic product is a skin cream.

* * * * *

UNITED STATES PATENT AND TRADEMARK OFFICE
CERTIFICATE OF CORRECTION

PATENT NO. : 8,580,362 B2
APPLICATION NO. : 10/579430
DATED : November 12, 2013
INVENTOR(S) : Van Den Heede et al.

It is certified that error appears in the above-identified patent and that said Letters Patent is hereby corrected as shown below:

On the title page, in the illustrative figure "transmisson" should read --transmission--.

In the Drawings:
Sheet 1 of 3 (Y Axis, FIGURE 1) line 1, Change "transmisson" to --transmission--.

In the Specification:
In column 1 line 21, Change "products" to --products.--.
In column 2 line 29, Change "polyamides" to --polyamides.--.
In column 2 line 50, Change "silicon-gel" to --silicone-gel--.
In column 4 lines 27-28, Change "footware." to --footwear.--.
In column 6 line 63, Change "textures" to --textures.--.
In column 7 line 53, Change "improve" to --improve.--.
In column 8 line 10, Change "23%" to --23%.--.
In column 8 line 17, Change "uv" to --UV--.
In column 8 line 33, Change "different" to --different.--.
In column 9 line 7, Change "embedment" to --embodiment--.
In column 9 line 8, After "known" insert --in--.
In column 10 line 27, Change "invention" to --invention.--.
In column 11 line 37, Change "polythelene" to --polyethylene--.
In column 11 lines 62-67, Delete "However, this.....embodiment." and insert the same on Col. 11, Line 61 as a continuation of the paragraph.
In column 13 line 7, Change "emulsion" to --emulsion.--.
In column 13 line 10, After "TEWL" delete "the".

Signed and Sealed this
Thirtieth Day of September, 2014

Michelle K. Lee
*Deputy Director of the United States Patent and Trademark Office*

CERTIFICATE OF CORRECTION (continued)
U.S. Pat. No. 8,580,362 B2

In column 13 line 65, Change "anathetic" to --anesthetic--.

In column 14 line 17, Change "sugar according" to --sugar. According--.

In column 15 line 22, After "silicone" delete "the".

In column 16 line 27, Change "calander" to --calender--.